(12) United States Patent
Huang et al.

(10) Patent No.: US 9,851,324 B1
(45) Date of Patent: Dec. 26, 2017

(54) SENSING APPARATUS AND MATERIAL SENSING METHOD

(71) Applicant: FINETEK Co., Ltd., New Taipei (TW)

(72) Inventors: Yin-Lun Huang, New Taipei (TW); I-Chu Lin, New Taipei (TW); Chao-Kai Cheng, New Taipei (TW); Yi-Liang Hou, New Taipei (TW)

(73) Assignee: Finetek Co., Ltd., New Taipei (TW)

( * ) Notice: Subject to any disclaimer, the term of this patent is extended or adjusted under 35 U.S.C. 154(b) by 0 days.

(21) Appl. No.: 15/395,153

(22) Filed: Dec. 30, 2016

(51) Int. Cl.
*G01N 27/22* (2006.01)

(52) U.S. Cl.
CPC .................................. *G01N 27/221* (2013.01)

(58) Field of Classification Search
CPC ... G01R 23/20; G01N 21/6408; H03H 19/008
See application file for complete search history.

(56) References Cited

U.S. PATENT DOCUMENTS

| | | | |
|---|---|---|---|
| 4,829,233 A | 5/1989 | Flemming et al. | |
| 5,334,941 A | 8/1994 | King | |
| 6,144,721 A * | 11/2000 | Stephens | H04M 1/24 324/520 |
| 2005/0124881 A1* | 6/2005 | Kanai | A61B 8/0858 600/437 |
| 2005/0182613 A1* | 8/2005 | Kwun | G01N 29/043 703/18 |
| 2010/0045309 A1 | 2/2010 | Zou et al. | |

* cited by examiner

*Primary Examiner* — Jermele M Hollington
*Assistant Examiner* — Alvaro Fortich
(74) *Attorney, Agent, or Firm* — Muncy, Geissler, Olds & Lowe, P.C.

(57) ABSTRACT

A sensing apparatus includes a probe and a sensing module. The sensing module includes a material sensing circuit, an operation unit and a signal output circuit. The sensing module generates a frequency sweep signal and sends the frequency sweep signal to the probe to sense a status of a material. The frequency sweep signal is a plurality of signals having different frequencies from each other in a predetermined frequency range. When the frequency sweep signal touches the material, an equivalent capacitance of the material is utilized to generate a reflected signal. The material sensing circuit receives the reflected signal and sends the reflected signal to the operation unit. The operation unit operates the reflected signal to generate a waveform signal to determine the status of the material. The operation unit utilizes an impedance spectrum to determine the status of the material.

14 Claims, 6 Drawing Sheets

SENSING APPARATUS AND MATERIAL SENSING METHOD

BACKGROUND OF THE INVENTION

Field of the Invention

The present invention relates to a sensing apparatus and a material sensing method, and especially relates to a sensing apparatus with variable frequency detection and a material sensing method with the variable frequency detection.

Description of the Related Art

Electrostatic capacity/radio frequency admittance sensors are used to detect the variant of the capacitance of the material. According to the capacitance equation $C=\epsilon A/d$, the electrostatic capacity/radio frequency admittance sensor converts the data from the physical signal into the electrical signal, wherein the data is sensed by the electrostatic capacity/radio frequency admittance sensor. When the electrostatic capacity/radio frequency admittance sensor is arranged in the tank or pipeline, the "A" (the material contact area) and "d" (the pole plate distance) are fixed, so that the variant of the "C" is influenced by the "$\epsilon$" (the permittivity of the material).

The electrostatic capacity/radio frequency admittance sensor transmits an alternating current signal with a fixed frequency to the probe, and then converts the capacitance into the electrical signal. When the material touches the probe, the variant of the signal intensity is generates. The control unit (the uC or the comparison circuit) of the related art electrostatic capacity/radio frequency admittance switch sensor sets a determination point. When the probe does not touch the material, the intensity of the feedback signal does not exceed the determination point. When the probe touches the material, the intensity of the feedback signal exceeds the determination point.

Moreover, after the electrostatic capacity/radio frequency admittance continuous sensor is installed, the electrostatic capacity/radio frequency admittance continuous sensor performs the two-point calibration. The values of the two points are inputted into the electrostatic capacity/radio frequency admittance continuous sensor, and then the control unit calculates the slope variant of the two points. Therefore, if the material is changed, according to the variant of the signal intensity, the equivalent volume of the material in the tank can be calculated. Then, the result can be displayed on the interface of the electrostatic capacity/radio frequency admittance continuous sensor, and the signal can be outputted to the back end system through, for examples, the RS-485 interface, the 4-20 mA interface, the Modbus interface and so on.

Below embodiment describes the related art method: After the sensor is installed, the material touching the probe in the tank is 10 cm, and the capacity ratio in the tank is 10%. At this time, the signal intensity is 100 mV. Then, the material touching the probe in the tank is changed as 50 cm, and the capacity ratio in the tank is 50%. At this time, the signal intensity is 500 mV. The capacity ratios mentioned above are inputted into the sensor. The control unit calculates to obtain the relationship between the capacity ratio and the signal intensity, namely, (50%−10%)/(500 mV−100 mV)=0.1 (%/mV). Therefore, when the signal intensity is changed as 600 mV, the capacity ratio in the tank being changed as 60% would be obtained on the sensor directly or through the output signal.

The permittivity of the material has different impedance responses due to the environmental variant (for examples, the temperature or the humidity), the quality degradation of the material (for examples, the difference of the moisture content) and the difference of the emitted frequencies of the sensor. However, the disadvantage of the related art electrostatic capacity/radio frequency admittance sensor is that the related art electrostatic capacity/radio frequency admittance sensor cannot operate in different frequencies but can only operate in the fixed frequency. Therefore, the possibility of the development of the intelligent and multi-functional measurement sensor is limited.

SUMMARY OF THE INVENTION

In order to solve the above-mentioned problems, an object of the present invention is to provide a sensing apparatus.

In order to solve the above-mentioned problems, an object of the present invention is to provide a material sensing method.

In order to achieve the object of the present invention mentioned above, the sensing apparatus of the present invention senses a varying status of a permittivity of a material. The sensing apparatus comprises a probe and a sensing module. The sensing module is connected to the probe. The sensing module comprises a material sensing circuit, an operation unit and a signal output circuit. The operation unit is electrically connected to the material sensing circuit. The signal output circuit is electrically connected to the operation unit.

The sensing module generates a frequency sweep signal and sends the frequency sweep signal to the probe to sense a status of the material. The frequency sweep signal is a plurality of signals having different frequencies from each other in a predetermined frequency range. When the frequency sweep signal touches the material, an equivalent capacitance of the material is utilized to generate a reflected signal. The material sensing circuit receives the reflected signal and sends the reflected signal to the operation unit. The operation unit operates the reflected signal to generate a waveform signal to determine the status of the material.

The operation unit utilizes an impedance spectrum to determine the status of the material. The impedance spectrum defines a plurality of status areas. Each of the status areas comprises different an output signal respectively. The operation unit applies signal intensity and a distribution frequency of the waveform signal to the impedance spectrum to determine a location of the waveform signal in the status areas, and performs a conversion accordingly to obtain a material equivalent volume and a material quality of the material and determines the status of the material. According to the location of the waveform signal in the status areas, the operation unit utilizes the signal output circuit to outwardly output the output signal of the status area for the location.

In order to achieve the object of the present invention mentioned above, the material sensing method of the present invention comprises following steps: A sensing apparatus is prepared, wherein the sensing apparatus measures a status of a material and comprises a probe and a sensing module which is connected to the probe. The probe is arranged in the material. The sensing apparatus performs an environmental calibration. The sensing module generates a frequency sweep signal and sends the frequency sweep signal to the probe to sense the status of the material, wherein the frequency sweep signal is a plurality of signals having different frequencies from each other in a predetermined frequency range.

When the frequency sweep signal touches the material, an equivalent capacitance of the material is utilized to generate a reflected signal. The sensing module operates the reflected signal to generate a waveform signal and performs a measurement mode to determine the status of the material to obtain a measurement result to outwardly output, wherein an impedance spectrum is utilized to determine the status of the material when performing the measurement mode, and the impedance spectrum defines a plurality of status areas, and each of the status areas comprises different an output signal respectively.

The sensing module applies signal intensity and a distribution frequency of the waveform signal to the impedance spectrum to determine a location of the waveform signal in the status areas, and performs a conversion accordingly to obtain a material equivalent volume and a material quality of the material and determines the status of the material. According to the location of the waveform signal in the status areas, the sensing module outwardly outputs the output signal of the status area for the location.

The advantage of the present invention is to provide an intelligent sensor with the variable frequency detection. Please refer to the detailed descriptions and figures of the present invention mentioned below for further understanding the technology, method and effect disclosed by the present invention to achieve the predetermined purpose of the present invention. The purpose, features and characteristics of the present invention can be understood well and in details. However, the figures are only for references and descriptions, but the present invention is not limited by the figures.

DETAILED DESCRIPTION OF THE INVENTION

Please refer to following detailed description and figures for the technical content of the present invention.

Figure 1:
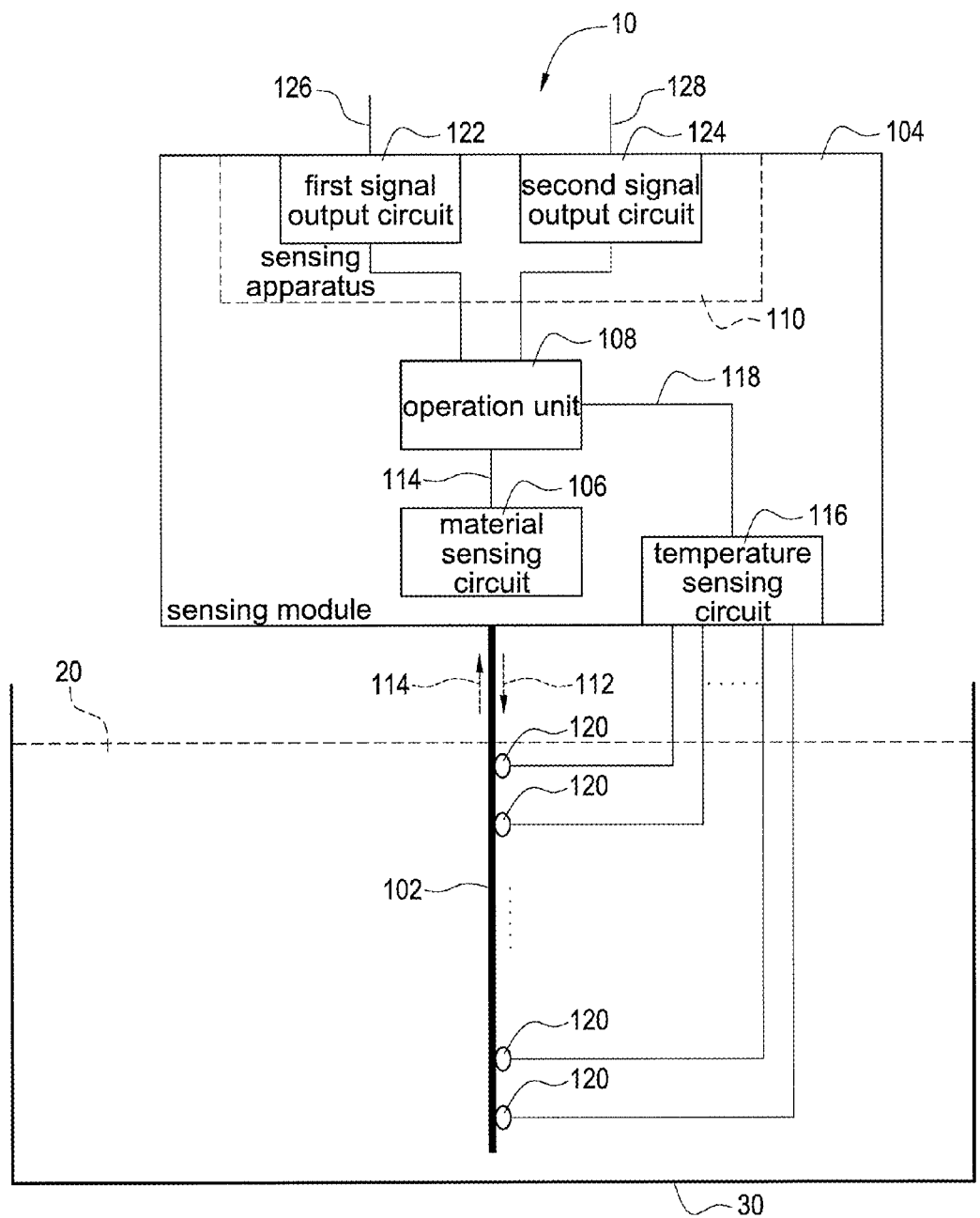
FIG. 1 shows a block diagram of an embodiment of the sensing apparatus of the present invention.

FIG. 1 shows a block diagram of an embodiment of the sensing apparatus of the present invention. A sensing apparatus 10 of the present invention senses a varying status of a permittivity of a material 20. The material 20 is arranged in a tank 30. The sensing apparatus 10 comprises a probe 102, a sensing module 104 and a plurality of temperature sensing units 120. The sensing module 104 comprises a material sensing circuit 106, an operation unit 108, a signal output circuit 110 and a temperature sensing circuit 116. The signal output circuit 110 comprises a first signal output circuit 122 and a second signal output circuit 124. The components mentioned above are electrically connected to each other. The sensing module 104 is connected to the probe 102. The temperature sensing units 120 are arranged on the probe 102 at regular intervals.

First, the sensing module 104 generates a frequency sweep signal 112 and then sends the frequency sweep signal 112 to the probe 102 to sense a status of the material 20. The frequency sweep signal 112 is a plurality of signals having different frequencies from each other in a predetermined frequency range. When the frequency sweep signal 112 touches the material 20, an equivalent capacitance of the material 20 is utilized to generate a reflected signal 114. The material sensing circuit 106 receives the reflected signal 114 and sends the reflected signal 114 to the operation unit 108. The operation unit 108 operates the reflected signal 114 to generate a waveform signal to determine the status of the material 20 (would be described in details later).

In another word, the first technical feature of the present invention is to provide an intelligent sensor with the variable frequency detection which is called an impedance spectrum sensor. The measuring principle of the impedance spectrum sensor is that the sensing module 104 transmits an alternating current signal with an adjustable frequency range (namely, the frequency sweep signal 112, for example but not limited, 50 MHz to 200 MHz) to the probe 102. A signal intensity of the alternating current signal is not changed due to the frequency variant, and the alternating current signal is a voltage with a fixed intensity. A structure and circuit of the probe 102 can be equivalent to a fixed equivalent inductance value (Ld), and a fixed equivalent capacitance value (Cd) is formed by the probe 102 touching the material 20. When the probe 102 does not touch the material 20, the medium of the probe 102 is the air, wherein the permittivity of the air is 1.

According to the sensing module 104 transmitting the frequency sweep signal 112, the operation unit 108 can draw the LdCd frequency response diagram of the probe 102 in the air and calculate the maximum impedance value at a certain frequency in the air (namely, the permittivity is 1), namely the resonance point (Fd). When the material 20 touches the probe 102, the equivalent capacitance value is changed as C1. At this time, the operation unit 108 re-calculates the resonance point as F1.

A predetermined value (A1) is written into the operation unit 108 of the impedance spectrum sensor. According to the F1 and A1 mentioned above, the present invention can design the continuous measurement sensor or point sensor. For example but not limited to, in the application of the point sensor, if the F1 is greater than the A1, the sensor outputs the signal. If the F1 is less than or equal to the A1, the sensor does not output the signal. Generally speaking, the permittivity of the material 20 is greater than 1, so the equivalent capacitance value which is generated should only increase, and thus the resonance point is smaller than the resonance point in the air.

Different material 20 has different permittivity, and the impedance spectrum sensor can measure the difference accurately. For example but not limited to, the material 20 is sensed as the engine oil originally, wherein its permittivity is E1. Due to long-term usage, the material 20 is metamorphic or has too many impurities, so that the permittivity of the material 20 is changed as E2. The impedance spectrum sensor can sense the changing of the resonance point to calculate and determine that the quality of the material 20 is changed. The impedance spectrum sensor can be, for example but not limited to, the oil conditioning sensor or the material conditioning sensor.

For another example, the material 20 is sensed as the corns originally, wherein the moisture content of the corns is 20% above. The impedance spectrum sensor sets the permittivity of the corns that the moisture content is 20% to 30% above is E3. When the impedance spectrum sensor senses that the moisture content of the corns is low (for example, lower than 15%), the permittivity of the corns is changed as E4. The changing can be measured by the impedance spectrum sensor. Such application is like the moisture instrument, but in the similar application, the variant of the permittivity of the material 20 is due to the change of the environment and time, but not the change of the volume.

Please refer to FIG. 1 again. The temperature sensing circuit 116 is used to detect an external environmental temperature (or the temperature of the sensing module 104) to generate a temperature sensing signal 118 and sends the temperature sensing signal 118 to the operation unit 108. Then, the operation unit 108 utilizes the temperature sensing signal 118 to perform a signal compensation for the waveform signal. Namely, in a signal compensation mode, the sensing module 104 generates the temperature sensing signal 118 to perform the signal compensation for the waveform signal.

Moreover, the temperature sensing units 120 is used to detect the external environmental temperature (or the temperature of the material 20) and inform the temperature sensing circuit 116 of the external environmental temperature, so that the temperature sensing circuit 116 generates the temperature sensing signal 118 and transmits the temperature sensing signal 118 to the operation unit 108. Then, the operation unit 108 utilizes the temperature sensing signal 118 to perform the signal compensation for the waveform signal. Namely, in the signal compensation mode, the sensing module 104 generates the temperature sensing signal 118 to perform the signal compensation for the waveform signal. The two signal compensations mentioned above can be arranged at different times, so they will not influence each other.

In another word, the second technical feature of the present invention is the signal compensation for the temperature. Because detecting the external environmental temperature results in the permittivity changing of the material 20 and characteristics changing of circuit boards and the semiconductor components on the circuit boards, the sensing module 104 needs the temperature compensation, so that the changing of the external environmental temperature does not influence the accuracy of the sensing module 104. Moreover, the influence for the material 20 due to the temperature changing has to be feed-backed to the operation unit 108, so the operation unit 108 can be aware of the temperature of the material 20 to perform the compensation for the permittivity changing. Therefore, the temperature sensing units 120 are arranged on the probe 102. The second technical feature of the present invention renders that the impedance spectrum sensor comprises another sensing ability to achieve the intelligent determination.

Please refer to FIG. 1 again. The operation unit 108 utilizes an impedance spectrum to determine the status of the material 20. The impedance spectrum defines a plurality of status areas. Each of the status areas comprises different an output signal respectively. The operation unit 108 applies a signal intensity and a distribution frequency of the waveform signal to the impedance spectrum to determine a location of the waveform signal in the status areas, and performs a conversion accordingly to obtain a material equivalent volume of the material 20 and a material quality of the material 20 and determines the status of the material 20. According to the location of the waveform signal in the status areas, the operation unit 108 utilizes the signal output circuit 110 to outwardly output the output signal of the status area for the location. The status areas comprise a measure area and a plurality of variation areas. The measure area is located in a pre-defined center frequency location. According to a plurality of predetermined signal intensity boundaries, the variation areas are distributed at two sides of the measure area respectively. The content mentioned above would be described in details later.

In accordance with the material equivalent volume, the operation unit 108 drives the first signal output circuit 122 to output a first signal 126. In accordance with the material quality, the operation unit 108 drives the second signal output circuit 124 to output a second signal 128. The output signal comprises the first signal 126 and the second signal 128. Signal types of the first signal 126 and the second signal 128 comprise following three kinds of types:

1. The first signal 126 is an analog signal and the second signal 128 is an analog signal. Namely, both the first signal 126 and the second signal 128 are analog signals.

2. The first signal 126 is a digital signal and the second signal 128 is a digital signal. Namely, both the first signal 126 and the second signal 128 are digital signals.

3. The first signal 126 is an analog signal and the second signal 128 is a digital signal, or the first signal 126 is a digital signal and the second signal 128 is an analog signal. Namely, one of the first signal 126 and the second signal 128 is an analog signal and the other is a digital signal.

Figure 2:
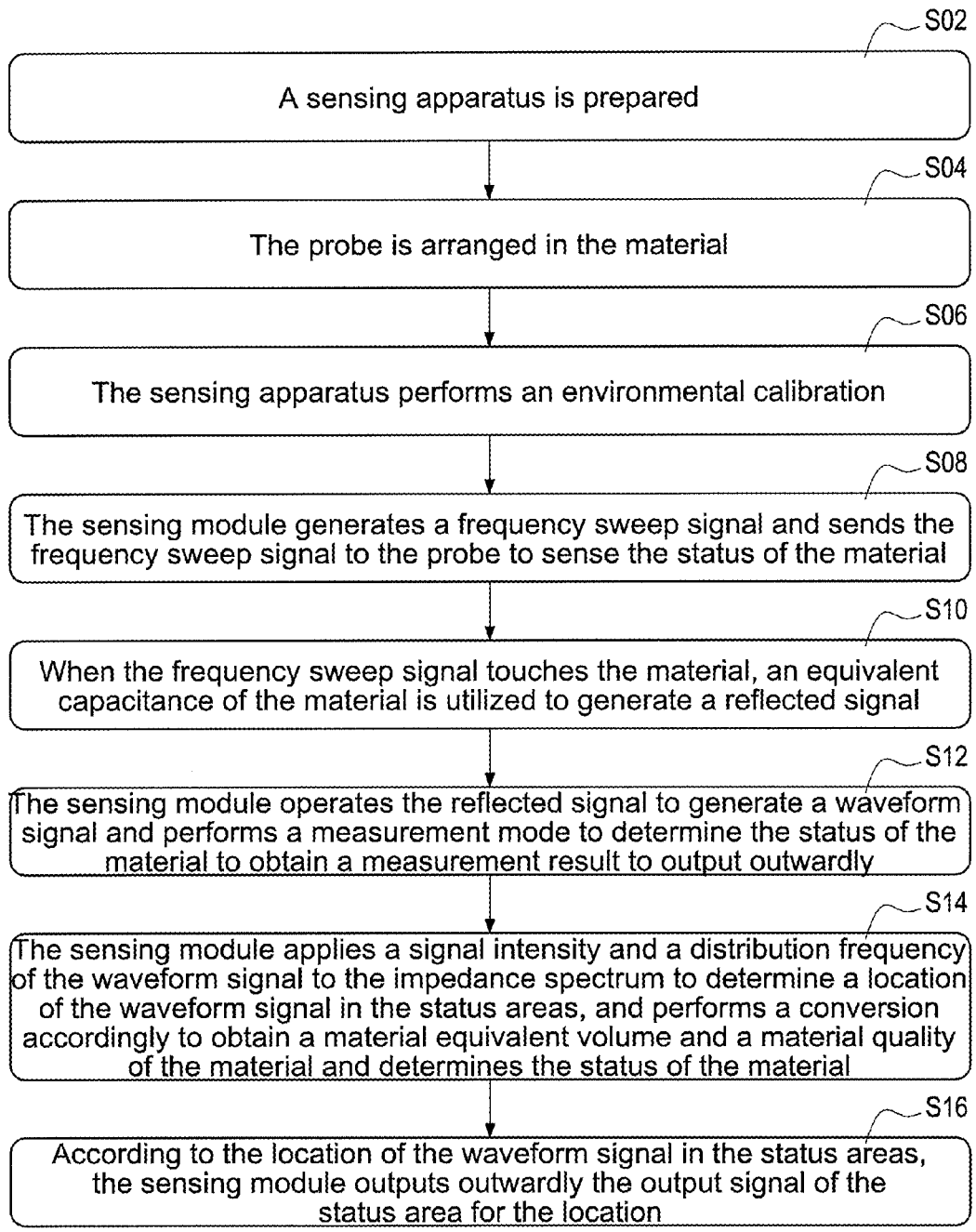
FIG. 2 shows a flow chart of an embodiment of the material sensing method of the present invention.

FIG. 2 shows a flow chart of an embodiment of the material sensing method of the present invention. A material sensing method of the present invention comprises following steps:

S02: A sensing apparatus is prepared, wherein the sensing apparatus measures a status of a material and comprises a probe and a sensing module which is connected to the probe. Then the material sensing method of the present invention goes to a step S04.

S04: The probe is arranged in the material. Then the material sensing method of the present invention goes to a step S06.

S06: The sensing apparatus performs an environmental calibration. Then the material sensing method of the present invention goes to a step S08.

S08: The sensing module generates a frequency sweep signal and sends the frequency sweep signal to the probe to sense the status of the material, wherein the frequency sweep signal is a plurality of signals having different frequencies from each other in a predetermined frequency range. Then the material sensing method of the present invention goes to a step S10.

S10: When the frequency sweep signal touches the material, an equivalent capacitance of the material is utilized to generate a reflected signal. Then the material sensing method of the present invention goes to a step S12.

S12: The sensing module operates the reflected signal to generate a waveform signal and performs a measurement mode to determine the status of the material to obtain a measurement result to outwardly output, wherein an impedance spectrum is utilized to determine the status of the material when performing the measurement mode, and the impedance spectrum defines a plurality of status areas, and each of the status areas comprises different an output signal respectively. Then the material sensing method of the present invention goes to a step S14.

S14: The sensing module applies signal intensity and a distribution frequency of the waveform signal to the impedance spectrum to determine a location of the waveform signal in the status areas, and performs a conversion accordingly to obtain a material equivalent volume and a material quality of the material and determines the status of the material. Then the material sensing method of the present invention goes to a step S16.

S16: According to the location of the waveform signal in the status areas, the sensing module outwardly outputs the output signal of the status area for the location.

The status areas comprise a measure area and a plurality of variation areas. The measure area is located in a pre-defined center frequency location. According to a plurality of predetermined signal intensity boundaries, the variation areas are distributed at two sides of the measure area respectively. The present invention is to set an operating mode and drives the sensing apparatus to perform a material volume measurement of the material or a material quality measurement of the material according to the operating mode, or to perform the material volume measurement of the material and the material quality measurement of the material simultaneously. The sensing module generates a first signal in accordance with a result of the material volume measurement to outwardly output the first signal. The sensing module generates a second signal in accordance with a result of the material quality measurement to outwardly output the second signal. The output signal comprises the first signal and the second signal.

Figure 3:
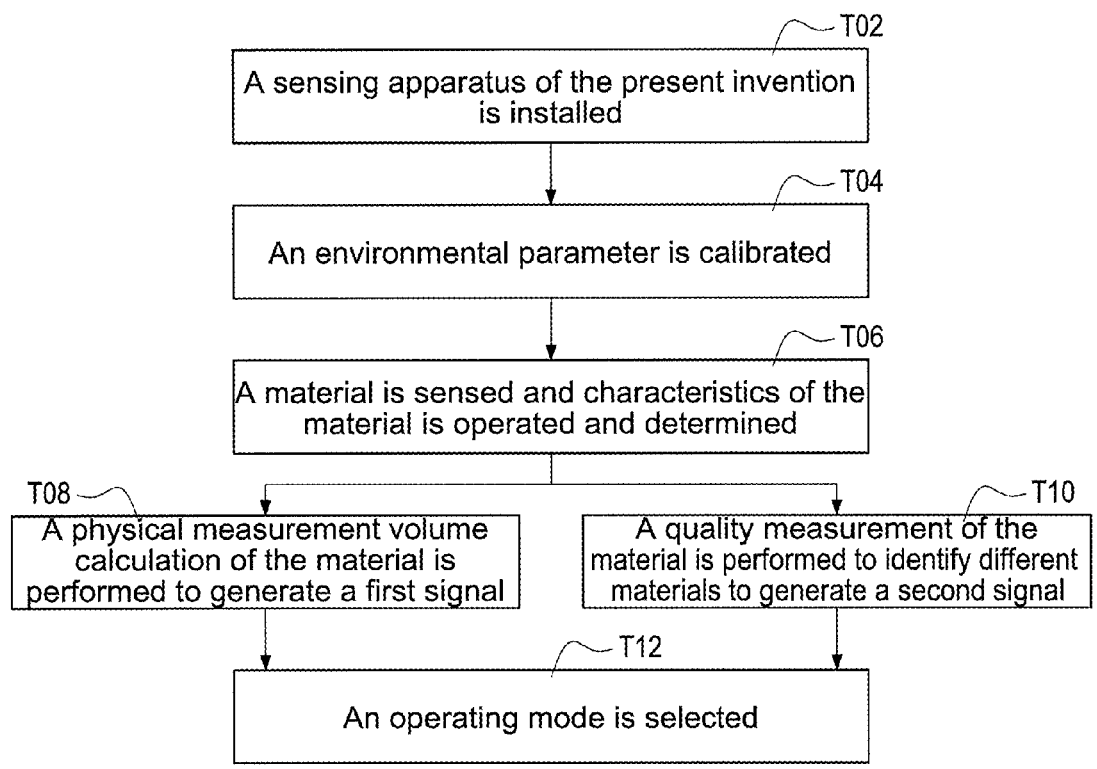
FIG. 3 shows a flow chart of another embodiment of the material sensing method of the present invention.

FIG. 3 shows a flow chart of another embodiment of the material sensing method of the present invention. A material sensing method of the present invention comprises following steps:

T02: A sensing apparatus of the present invention is installed. Then the material sensing method of the present invention goes to a step T04.

T04: An environmental parameter is calibrated. Then the material sensing method of the present invention goes to a step T06.

T06: A material is sensed and characteristics of the material is operated and determined. Then the material sensing method of the present invention goes to a step T08 or a step T10.

T08: A physical measurement volume calculation of the material is performed to generate a first signal. Then the material sensing method of the present invention goes to a step T12.

T10: A quality measurement of the material is performed to identify different materials to generate a second signal. Then the material sensing method of the present invention goes to a step T12.

T12: An operating mode is selected. The material sensing method of the present invention can select one single signal output or a plurality of the signals outputs of any combinations by the first signal and the second signal. Then, the output circuit converts the signals into signals of the current analog or digital communication interfaces according to the operating mode, wherein the current analog or digital communication interfaces are, for examples but not limited to, the wireless HART interface, the RS-485 interface, the 4-20 mA interface, the IO-Link interface and so on.

In another word, the third technical feature of the present invention is to provide a determination method to think comprehensively and determine the variant of the permittivity of the material, the variant of the temperature and the variant of the volume of the material to design a determination equation: Curve(x)=f(T'ϵ)+I(T'ϵ'V), wherein the symbol "f" indicates the transmitting frequency, the symbol "I" indicates the feedback signal intensity, the symbol "T" indicates the temperature, the symbol "ϵ" indicates the permittivity of the material, and the symbol "V" indicates the volume of the material.

Figure 4:
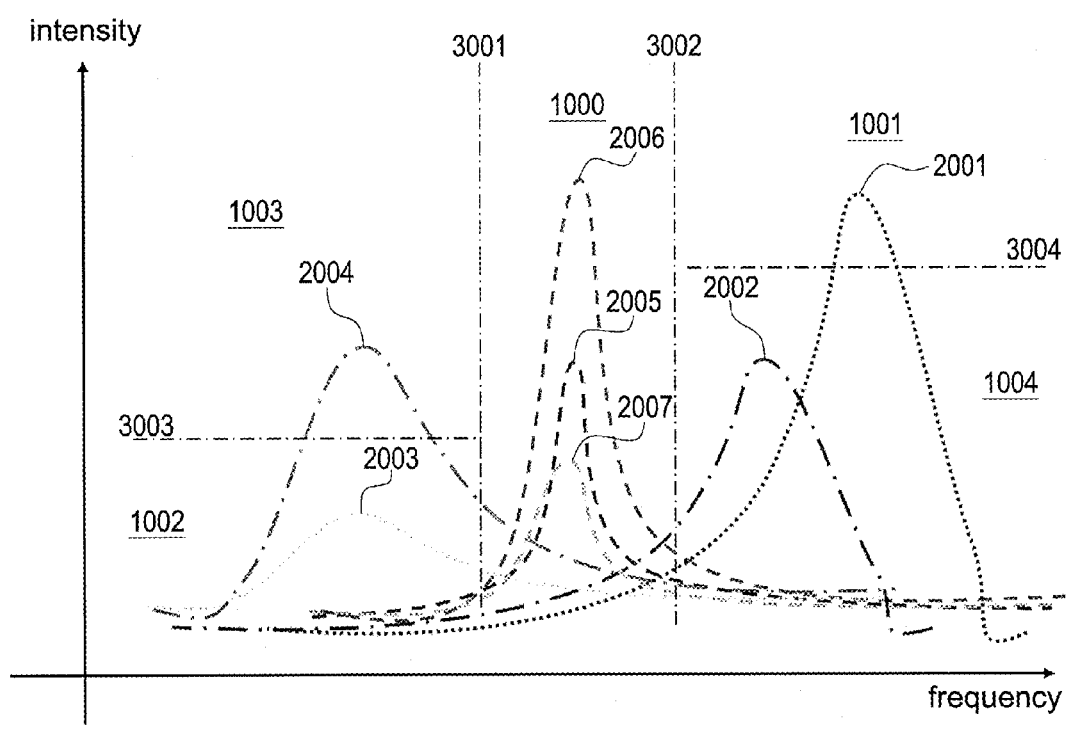
FIG. 4 shows a waveform diagram of the impedance spectrum of the present invention.
Figure 5:
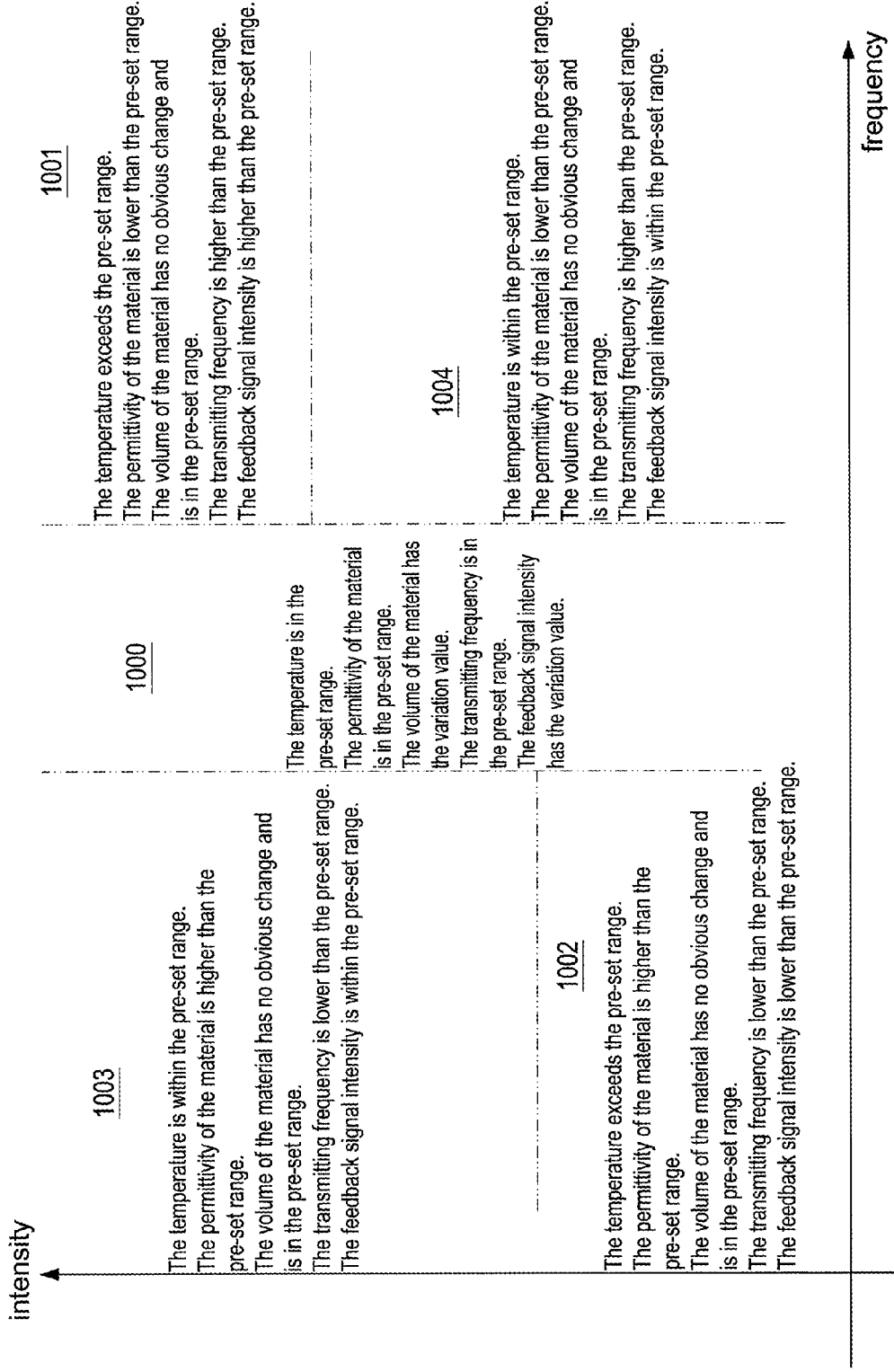
FIG. 5 shows the status areas of the present invention.

FIG. 4 shows a waveform diagram of the impedance spectrum of the present invention. FIG. 5 shows the status areas of the present invention. FIG. 4 comprises seven curves (namely, seven waveform signals measured in seven different statuses respectively). They are a first waveform signal 2001, a second waveform signal 2002, a third waveform signal 2003, a fourth waveform signal 2004, a fifth waveform signal 2005, a sixth waveform signal 2006 and a seventh waveform signal 2007. In FIG. 4 and FIG. 5, the unit of the frequency is hertz while the unit of the intensity is not limited and can be any unit.

According to the determination equation mentioned above, FIG. 4 and FIG. 5, the impedance spectrum can be divided into five status areas comprising a measure area 1000 and four variation areas, wherein the four variation areas comprise a first variation area 1001, a second variation area 1002, a third variation area 1003 and a fourth variation area 1004. The measure area 1000 is located in a pre-defined center frequency location. According to a plurality of predetermined signal intensity boundaries (which comprise a first predetermined signal intensity boundary 3001, a second predetermined signal intensity boundary 3002, a third predetermined signal intensity boundary 3003 and a fourth predetermined signal intensity boundary 3004), the variation areas (namely, the first variation area 1001, the second variation area 1002, the third variation area 1003 and the fourth variation area 1004) are distributed at two sides of the measure area 1000 respectively.

In the measure area 1000: The temperature is in the pre-set range. The permittivity of the material is in the pre-set range. The volume of the material has the variation value. The transmitting frequency is in the pre-set range. The feedback signal intensity has the variation value. In this mode, it usually belongs to pre-defining the measuring area of the variation of the volume of the material.

In another word, a maximum value of the signal intensity of the waveform signal is defined as an intensity maximum value. When a frequency of the intensity maximum value is between a first frequency and a second frequency (for examples, the fifth waveform signal 2005, the sixth waveform signal 2006 and the seventh waveform signal 2007 shown in FIG. 4), the external environmental temperature is determined as in a pre-set temperature range, the permittivity of the material is determined as in a pre-set permittivity range, the material equivalent volume of the material is determined as exceeding a pre-set volume range and a signal intensity of the reflected signal is determined as exceeding a pre-set reflected intensity range, wherein the second frequency is greater than the first frequency.

In the first variation area 1001: The temperature exceeds the pre-set range. The permittivity of the material is lower than the pre-set range. The volume of the material has no obvious change and is in the pre-set range. The transmitting frequency is higher than the pre-set range. The feedback signal intensity is higher than the pre-set range. In this mode (the temperature is changing and the material is changing), it usually belongs to an area that the volume does not change but the quality of the material changes (namely, the material is changed as different material or the quality of the material changes).

In another word, when the frequency of the intensity maximum value is greater than the second frequency and the intensity maximum value is greater than a first intensity predetermined value (for example, the first waveform signal 2001 shown in FIG. 4), the external environmental temperature is determined as exceeding the pre-set temperature range, the permittivity of the material is determined as lower than the pre-set permittivity range, the material equivalent volume of the material is determined as within the pre-set volume range and the signal intensity of the reflected signal is determined as exceeding the pre-set reflected intensity range, but the material quality of the material is determined as changing.

In the second variation area 1002: The temperature exceeds the pre-set range. The permittivity of the material is higher than the pre-set range. The volume of the material has no obvious change and is in the pre-set range. The transmitting frequency is lower than the pre-set range. The feedback signal intensity is lower than the pre-set range. In this mode (the temperature is changing and the material is changing), it usually belongs to an area that the volume does not change but the quality of the material changes (namely, the material is changed as different material or the quality of the material changes).

In another word, when the frequency of the intensity maximum value is less than the first frequency and the intensity maximum value is not greater than a second intensity predetermined value (for example, the third waveform signal 2003 shown in FIG. 4), the external environmental temperature is determined as exceeding the pre-set temperature range, the permittivity of the material is determined as higher than the pre-set permittivity range, the material equivalent volume of the material is determined as within the pre-set volume range and the signal intensity of the reflected signal is determined as lower than the pre-set reflected intensity range, but the material quality of the material is determined as changing.

In the third variation area 1003: The temperature is within the pre-set range. The permittivity of the material is higher than the pre-set range. The volume of the material has no obvious change and is in the pre-set range. The transmitting frequency is lower than the pre-set range. The feedback signal intensity is within the pre-set range. In this mode (the material is changing), it usually belongs to an area that the volume does not change but the quality of the material changes (namely, the material is changed as different material or the quality of the material changes).

In another word, when the frequency of the intensity maximum value is less than the first frequency and the intensity maximum value is greater than the second intensity predetermined value (for example, the fourth waveform signal 2004 shown in FIG. 4), the external environmental temperature is determined as within the pre-set temperature range, the permittivity of the material is determined as higher than the pre-set permittivity range, the material equivalent volume of the material is determined as within the pre-set volume range and the signal intensity of the reflected signal is determined as within the pre-set reflected intensity range, but the material quality of the material is determined as changing.

In the fourth variation area 1004: The temperature is within the pre-set range. The permittivity of the material is lower than the pre-set range. The volume of the material has no obvious change and is in the pre-set range. The transmitting frequency is higher than the pre-set range. The feedback signal intensity is within the pre-set range. In this mode (the material is changing), it usually belongs to an area that the volume does not change but the quality of the material changes (namely, the material is changed as different material or the quality of the material changes).

In another word, when the frequency of the intensity maximum value is greater than the second frequency and the intensity maximum value is not greater than the first intensity predetermined value (for example, the second waveform signal 2002 shown in FIG. 4), the external environmental temperature is determined as within the pre-set temperature range, the permittivity of the material is determined as lower than the pre-set permittivity range, the material equivalent volume of the material is determined as within the pre-set volume range and the signal intensity of the reflected signal is determined as within the pre-set reflected intensity range, but the material quality of the material is determined as changing.

Therefore, the third technical feature of the present invention is to comprehensively determine the variant of the permittivity of the material, the variant of the environmental temperature and the variant of the volume of the material according to the pre-definition of the five areas mentioned above.

Figure 6:
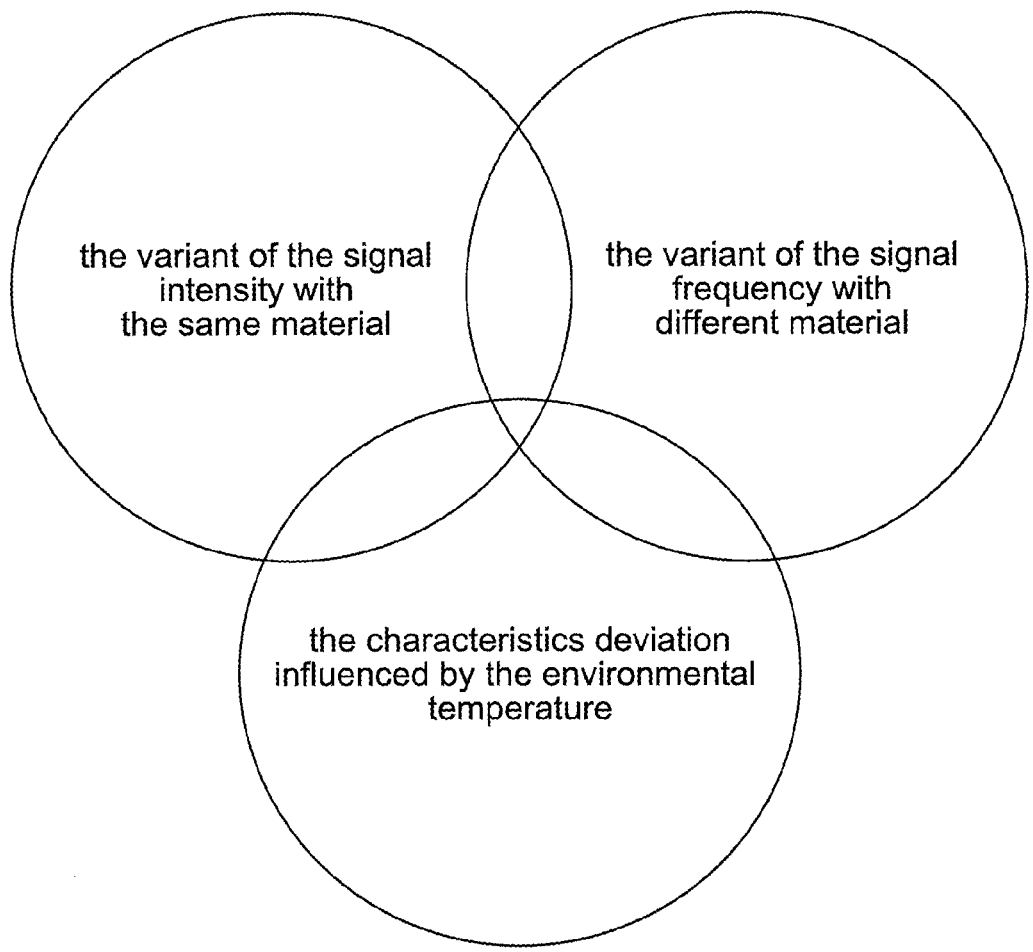
FIG. 6 shows the concepts of the present invention.

FIG. 6 shows the concepts of the present invention. The present invention can comprehensively determine the variant of the signal intensity with the same material, the variant of the signal frequency with different material and the characteristics deviation influenced by the environmental temperature. In conclusion, utilizing the frequency sweep principle of the impedance spectrum sensor, the method for determining the intensity by the electrostatic capacity/radio frequency admittance sensor, the probe structure of the continuous sensor and the compensation circuit considering the influence of the environmental temperature, the present invention provides a contact-type multi-functional continuous sensing apparatus that can measure the material volume in the tank and can determine the quality of the material at the same time but is not influenced by the variant of the environmental temperature.

The principles of both the impedance spectrum sensor and the electrostatic capacity/radio frequency admittance sensor regard the material in the installed environment as an equivalent capacitance value. The probe of the sensor detects the variation of the equivalent capacitance value to perform outputting and responding. The variation of the equivalent capacitance value depends on the permittivity of the material. If the permittivity of the material is greater, the variation is greater. If the permittivity of the material is less, the variation is less. The electrostatic capacity/radio frequency admittance continuous sensor performs the calculation of the probe touching the area with the material to determine the volume of the material in the tank. Other sensing apparatuses have to be installed to detect whether the quality of the material is changing or not in the measurement, so that the efficiency of monitoring the volume and the quality of the material in the tank can be achieved.

The present invention combines the principle of the impedance spectrum sensor with the principle of the electrostatic capacity/radio frequency admittance sensor. Utilizing the adjustable frequency signal and the probe structure design of the contact-type continuous sensor, the present invention senses and obtains the frequency response characteristics of the feedback signal from the material to analyze the variant of the signal frequency and the signal intensity, and performs the compensation for the circuit and the material due to the environmental temperature. The present invention determines the variant of the material in the tank, verifies the quality of the material and detects the temperature of the material, and then displays the results on the user interface of the sensing module or outputs the results to the central control system through the interfaces (for examples but not limited to, the wireless HART interface, the RS-485 interface, the 4-20 mA interface, the IO-Link interface and so on).

Namely, the present invention utilizes the sensing module to sense the frequency variant and the intensity variant of the reflected signal. According to the pre-defined permittivity of the material and the compensation for the environmental temperature variant, utilizing the dual determination mode, the present invention outputs the determination result through the output circuit and the interfaces (for examples but not limited to, the wireless HART interface, the RS-485 interface, the 4-20 mA interface, the IO-Link interface and so on), so that the signal frequency deviation curvature and the signal intensity variant can be obtained. Therefore, the present invention calculates the height of the material (namely, the volume of the material) and the quality of the material. Moreover, the present invention can select the single mode measurement (material level) or the multi-functional measurement mode (material quality determination).

Although the present invention has been described with reference to the preferred embodiment thereof, it will be understood that the invention is not limited to the details thereof. Various substitutions and modifications have been suggested in the foregoing description, and others will occur to those of ordinary skill in the art. Therefore, all such substitutions and modifications are intended to be embraced within the scope of the invention as defined in the appended claims.

What is claimed is:

1. A sensing apparatus sensing a varying status of a permittivity of a material, the sensing apparatus comprising:
   a probe; and
   a sensing module connected to the probe,
   wherein the sensing module comprises:
   a material sensing circuit;
   an operation unit electrically connected to the material sensing circuit; and
   a signal output circuit electrically connected to the operation unit,
   wherein the sensing module generates a frequency sweep signal and sends the frequency sweep signal to the probe to sense a status of the material; the frequency sweep signal is a plurality of signals having different frequencies from each other in a predetermined frequency range; when the frequency sweep signal touches the material, an equivalent capacitance of the material is utilized to generate a reflected signal; the material sensing circuit receives the reflected signal and sends the reflected signal to the operation unit; the operation unit operates the reflected signal to generate a waveform signal to determine the status of the material;
   wherein the operation unit utilizes an impedance spectrum to determine the status of the material; the impedance spectrum defines a plurality of status areas; each of the status areas comprises different an output signal respectively; the operation unit applies a signal intensity and a distribution frequency of the waveform signal to the impedance spectrum to determine a location of the waveform signal in the status areas, and performs a conversion accordingly to obtain a material equivalent volume and a material quality of the material and determines the status of the material; according to the location of the waveform signal in the status areas, the operation unit utilizes the signal output circuit to outwardly output the output signal of the status area for the location.

2. The sensing apparatus in claim 1, wherein the status areas comprise a measure area and a plurality of variation areas; the measure area is located in a pre-defined center frequency location; according to a plurality of predetemined signal intensity boundaries, the variation areas are distributed at two sides of the measure area respectively.

3. The sensing apparatus in claim 1, wherein the sensing module further comprises:
   a temperature sensing circuit electrically connected to the operation unit,
   wherein the temperature sensing circuit generates a temperature sensing signal and sends the temperature sensing signal to the operation unit; the operation unit utilizes the temperature sensing signal to perform a signal compensation for the waveform signal.

4. The sensing apparatus in claim 3, wherein the temperature sensing circuit is used to detect an external environmental temperature to generate the temperature sensing signal.

5. The sensing apparatus in claim 3 further comprising:
   a plurality of temperature sensing units, the temperature sensing units arranged on the probe at regular intervals and electrically connected to the temperature sensing circuit respectively,
   wherein the temperature sensing units are used to detect an external environmental temperature.

6. The sensing apparatus in claim 1, wherein the signal output circuit comprises:
   a first signal output circuit electrically connected to the operation unit; and
   a second signal output circuit electrically connected to the operation unit,
   wherein in accordance with the material equivalent volume, the operation unit drives the first signal output circuit to output a first signal; in accordance with the material quality, the operation unit drives the second signal output circuit to output a second signal; the output signal comprises the first signal and the second signal.

7. The sensing apparatus in claim 6, wherein the first signal is an analog signal and the second signal is an analog signal.

8. The sensing apparatus in claim 6, wherein the first signal is a digital signal and the second signal is a digital signal.

9. The sensing apparatus in claim 6, wherein the first signal is an analog signal and the second signal is a digital signal, or the first signal is a digital signal and the second signal is an analog signal.

10. The sensing apparatus in claim 7, wherein in a signal compensation mode, the sensing module generates a temperature sensing signal to perform a signal compensation for the waveform signal.

11. A material sensing method comprising:
    preparing a sensing apparatus, wherein the sensing apparatus measures a status of a material and comprises a probe and a sensing module connected to the probe;
    arranging the probe in the material;
    performing an environmental calibration to the sensing apparatus;
    generating a frequency sweep signal and sending the frequency sweep signal to the probe to sense the status of the material by the sensing module, wherein the frequency sweep signal is a plurality of signals having different frequencies from each other in a predetermined frequency range;

utilizing an equivalent capacitance of the material to generate a reflected signal when the frequency sweep signal touches the material;

operating the reflected signal to generate a waveform signal and performing a measurement mode to determine the status of the material to obtain a measurement result to outwardly output by the sensing module, wherein an impedance spectrum is utilized to determine the status of the material when performing the measurement mode, and the impedance spectrum defines a plurality of status areas, and each of the status areas comprises different an output signal respectively;

applying a signal intensity and a distribution frequency of the waveform signal to the impedance spectrum to determine a location of the waveform signal in the status areas, and performing a conversion accordingly to obtain a material equivalent volume and a material quality of the material and determining the status of the material by the sensing module; and outputting outwardly the output signal of the status area for the location by the sensing module according to the location of the waveform signal in the status areas.

12. The material sensing method in claim 11, wherein the status areas comprise a measure area and a plurality of variation areas; the measure area is located in a pre-defined center frequency location; according to a plurality of pre-determined signal intensity boundaries, the variation areas are distributed at two sides of the measure area respectively.

13. The material sensing method in claim 11 further comprising:

setting an operating mode and driving the sensing apparatus to perform a material volume measurement of the material or a material quality measurement of the material according to the operating mode, or to perform the material volume measurement of the material and the material quality measurement of the material simultaneously.

14. The material sensing method in claim 11, wherein the sensing module generates a first signal in accordance with a result of the material volume measurement to outwardly output the first signal; the sensing module generates a second signal in accordance with a result of the material quality measurement to outwardly output the second signal; the output signal comprises the first signal and the second signal.

* * * * *